United States Patent [19]

Wilson et al.

[11] Patent Number: 5,425,941
[45] Date of Patent: Jun. 20, 1995

[54] **BIOLOGICAL CONTROL OF DISEASES OF HARVESTED AGRICULTURAL COMMODITIES USING STRAINS OF THE YEAST *CANDIDA OLEOPHOLA***

[75] Inventors: Charles L. Wilson, Frederick, Md.; Michael E. Wisniewski, Shepherdstown, W. Va.; Edo Chalutz, Rishon le 'Zion, Israel

[73] Assignee: The United States of America as represented by the Secretary of Agriculture, Washington, D.C.

[21] Appl. No.: 136,182

[22] Filed: Oct. 15, 1993

Related U.S. Application Data

[63] Continuation-in-part of Ser. No. 745,796, Aug. 16, 1991, abandoned.

[51] Int. Cl.$^6$ .................. A01N 63/00; C12N 1/16
[52] U.S. Cl. .................. 424/93.51; 435/255.4; 435/921
[58] Field of Search .................. 435/255.4, 921; 424/93 S, 93.51

[56] References Cited

U.S. PATENT DOCUMENTS

| | | | |
|---|---|---|---|
| 4,764,371 | 8/1988 | Pusey et al. | 424/93 |
| 4,857,468 | 8/1989 | Kutsuki | 435/280 |
| 5,041,384 | 8/1991 | Wilson et al. | 435/255.4 |
| 5,047,239 | 9/1991 | Pusey | 424/93 |

OTHER PUBLICATIONS

McLaughlin et al., "Effect of Inoculum Concentration and Salt Solutions on Biological Control of Postharvest Diseases of Apple with *Candida* sp.,") *Phytopathology*, vol. 80, No. 5, pp. 456–461. 1990.

McLaughlin et al., "Characterization and Reclassification of Yeasts Used for Biological Control of Postharvest Diseases of Fruits and Vegetables", *Applied and Environmental Microbiology*, vol. 56, No. 11, pp. 3583–3586, 1990.

Parish et al., "Yeasts and Molds Isolated from Spoiling Citrus Products and By–products", *Biological Abstracts* 89:289183, 1989.

Davis et al., "The Fungal Flora of Loganberries in Relation to Storage and Spoilage", *Biological Abstracts*; 77:179654, 1977.

Pusey et al., "Compatibility of *Bacillus subtilis* for Postharvest Control of Peach Brown Rot with Commercial Fruit Waxes, Dicloran, and Cold Storage Conditions", *Plant Disease*, vol. 70, No. 6, pp. 587–590, 1986.

Pusey et al., "Postharvest Biological Control of Stone Fruit Brown Rot by *Bacillus subtilis, Plant Disease*", vol. 68, No. 9, pp. 753–756, 1984.

Wilson et al., "Biological Control of Postharvest Diseases of Fruits and Vegetables: An Emerging Technology", *Ann. Rev. Phytopathol.*, vol. 27, pp. 425–441, 1989.

Droby et al., "Antagonistic Microorganisms as Biological Control Agents of Postharvest Diseases of Fruits and Vegetables", *Postharvest News and Information*, vol. 2, pp. 169–173, 1991.

*Primary Examiner*—Marian C. Knode
*Assistant Examiner*—Kristin Larson
*Attorney, Agent, or Firm*—Howard Silverstein; John Fado; Janelle S. Graeter

[57] ABSTRACT

The present invention is drawn to isolates of *Candida oleophila* which are effective for the control of postharvest diseases in fruit and to biocontrol compositions which include such isolates. A method of utilizing the isolates to inhibit pathogens which cause postharvest diseases is also described. The organisms were isolated from the surface of tomato fruit and are useful for the control of a variety of fruit-rot pathogens in a variety of fruits.

10 Claims, 3 Drawing Sheets

BIOLOGICAL CONTROL OF DISEASES OF HARVESTED AGRICULTURAL COMMODITIES USING STRAINS OF THE YEAST *CANDIDA OLEOPHOLA*

This application is a continuation-in-part of application Ser. No. 07/745,796, filed Aug. 16, 1991 herein incorporated by reference, now abandoned.

BACKGROUND OF THE INVENTION

1. Field of the Invention

The present invention relates to the biological control of postharvest diseases in fruit. More particularly, this invention relates to a method for biologically controlling postharvest rots on fruit using strains of *Candida oleophila* (*C. oleophila*).

2. Description of the Prior Art

Postharvest diseases of fruit cause 15 to 25% losses yearly in the fruit industry worldwide. Fungicides, the major means for combating these diseases, are often ineffective and pose hazards to humans and the environment. Therefore, a critical need exists for new methods to control postharvest diseases.

Recently, it has been shown that the postharvest treatment of fruit with antagonistic microorganisms is an effective approach to the control of postharvest rot. Remarkable success was shown in the control of brown rot in peaches caused by *Monilinia fructicola* with the bacterium *Bacillus subtilis* (Pusey et al., *Plant Dis.*, 86: 753–756, 1986), and the yeast *Pichia guilliermondii* has been shown to control a variety of postharvest rots of fruits and vegetables (Droby et al., *Postharvest News and Information*, 2: 169–173, 1991). A review of this subject can be found in *Annual Reviews* (Wilson and Wisniewski, *Annual Review of Plant Pathology*, 27: 425–441, 1989).

SUMMARY OF THE INVENTION

We have discovered that strains of *C. oleophila* are highly effective in controlling a variety of fruit-rot pathogens which affect several species of fruit. As a preferred embodiment, three isolates of the new strains have been deposited with the culture collection of the Northern Regional Research Center, U.S. Department of Agriculture, Peoria, Ill. 61604, under the acquisition numbers NRRL Y-18844, NRRL Y-18845 and NRRL Y-18846. The deposited materials have been accepted for deposit under the Budapest Treaty on the International Recognition of the Deposit of Microorganisms for the purpose of patent procedures. Further, (1) said depository affords permanence of the deposits and ready accessibility thereto by the public if a patent is granted, (2) the materials have been deposited under conditions that assure that access to the material will be available during the pendency of the patent application to one determined by the Commissioner of Patents and Trademarks to be entitled thereto under 37 CFR 1.14 and 35 USC 122. All restrictions on the availability of progenies of the strain to the public will be irrevocably removed upon the granting of the patent. These isolates have been identified as *Candida oleophila* Montrocher by the Centraalbureau voor Schimmelcultures in the Netherlands and the German Collection of Microorganisms and Cell Cultures, Federal Republic of Germany.

Accordingly, it is an object of the present invention to provide a novel biological control agent which is safe and highly effective for the control of a variety of postharvest diseases in a variety of fruits.

It is also an object of the invention to provide a method of biologically controlling postharvest diseases in fruit which eliminates the use of fungicidal treatments.

In accordance with our invention, fruits are subjected to a composition comprised of at least one isolate of *C. oleophila* having the identifying characteristics of *C. oleophila* NRRL Y-NRRL Y-18844, NRRL Y-18845 and NRRL Y-18846. In effect, the organisms multiply and occupy the surfaces of fruit wounds, thereby preventing infection by fruit-rot pathogens.

DESCRIPTION OF THE PREFERRED EMBODIMENTS

Figure 1:
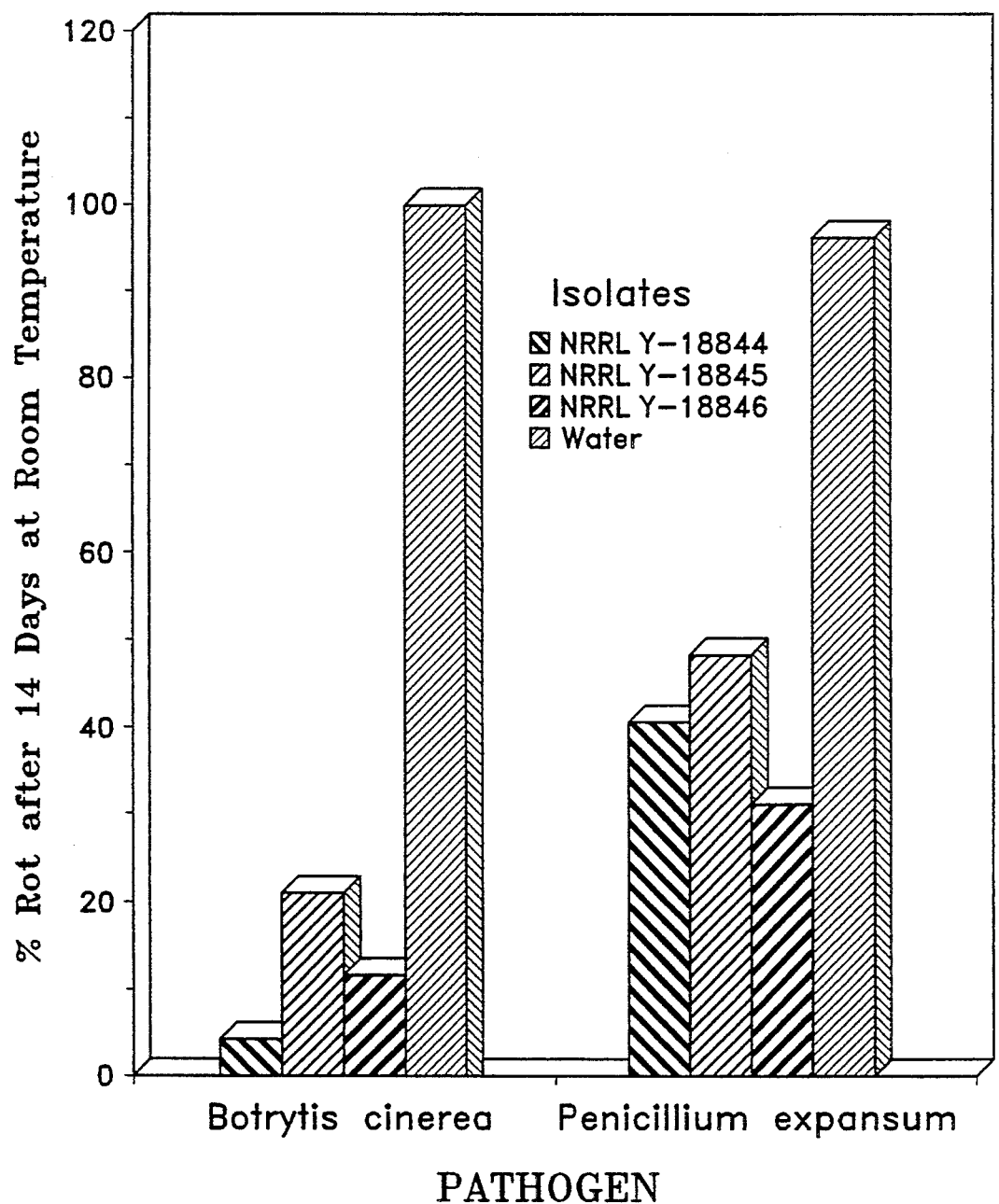
FIG. 1 is a bar graph of percent rot of apples treated with NRRL Y-18844, NRRL Y-18845 and NRRL Y-18846 and water and challenged with the rot organisms *Botrytis cinerea* and *Penicillium expansum*.

Isolates NRRL Y-18844, NRRL Y-18845 and NRRL Y-18846 were obtained from the surface of tomato fruit by repeatedly washing the fruit with sterile water. The organisms are thereafter

TABLE 1

| | Isolate Number | | |
|---|---|---|---|
| | NRRL Y-18844 | NRRL Y-18845 | NRRL Y-18846 |
| GROWTH | | | |
| D-glucose | + | + | + |
| D-galactose | − | − | + |
| L-sorbose | + | + | + |
| D-glucosamine | + | + | + |
| D-ribose | − | − | − |
| D-xylose | +$^W$ | +$^W$ | + |
| L-arabinose | − | − | − |
| L-rhamnose | − | − | − |
| sucrose | + | + | + |
| maltose | + | + | + |
| α,α trehalose | + | + | + |
| methyl α-glucoside | − | − | − |
| cellobiose | + | + | − |
| melibiose | − | − | − |
| lactose | − | − | − |
| raffinose | − | − | − |
| melezitose | + | + | + |
| glycerol | + | + | + |
| meso-erythritol | − | − | − |
| D-glucitol | + | + | + |
| myo-inositol | − | − | − |
| 2-keto-D-gluconate | + | + | + |
| D-gluconate | − | − | − |
| D-glucuronate | − | − | − |
| DL-lactate | − | − | − |
| FERMENTATION | | | |
| glucose | + | + | + |
| galactose | − | − | + |
| maltose | − | − | − |
| sucrose | vw | vw | − |
| lactose | − | − | − |
| raffinose | − | − | − |
| nitrate | − | − | − |
| ethylamine | + | + | + |

TABLE 1-continued

| | Isolate Number | | |
|---|---|---|---|
| | NRRL Y-18844 | NRRL Y-18845 | NRRL Y-18846 |
| L-Lysine | + | + | + |
| cadaverine | + | + | + |
| TEMPERATURE | | | |
| at 37° C. | − | − | − |
| ANTIBIOTICS | | | |
| 01% cycloheximide | +[w] | − | + |

[w] = weak;
[vw] = very weak plated and grown on any nutritionally rich medium sufficient to support growth of microorganisms. Preferably, the medium is either yeast dextrose agar (NYDA) or yeast-malt extract agar (YM).

Isolates NRRL Y-18844, NRRL 18845 and NRRL Y-18846 have the following identifying characterisitcs: colonies are cream white, slightly raised, shiny, round and smooth. Pseudohyphae were observed. Characteristics observed during biochemical and phsiological tests are presented in Table 1.

Growth of the organisms is effected under aerobic conditions at any temperature satisfactory for growth of the organism; i.e. from about 10° C. to about 30° C. The preferred temperature range is about 20° C. to 25° C. The pH of the nutrient medium is about neutral; i.e. 6.7 to 7.2. The incubation time is that time necessary for the organisms to reach a stationary phase of growth. Incubation time is preferably from about 40 to 60 hours.

Isolates NRRL Y-18844, NRRL Y-18845 and NRRL Y-18846 may be grown in any conventional shake flask for small fermentation runs. For large scale operations, it is convenient to carry out the culture in a fermentation tank while applying agitation and aeration to the inoculated liquid medium. Following incubation, the organisms are harvested by conventional sedimentary methodology; i.e. centrifugation or filtration. Cultures are stored on silica gel and frozen until used.

Isolates NRRL Y-18844, NRRL Y-18845 and NRRL Y-18846 are useful for the control of a variety of fruit-rot pathogens, including but not limited to, *Penicillium digitatum, Botrytis cinerea, Rhizopus stolinifer, Penicillium expansum* and *Monilinia fructicola*.

The organisms of the invention are useful for the control of postharvest diseases in a variety of fruits including, but not limited to, all cultivars of citrus fruits, grapes, apples, pears, tomatoes, persimmons and the like. Suitable citrus fruits include, but are not limited to, grapefruits, oranges, lemons and the like.

The organisms of the invention are preferably applied to the fruits in suspension with water or any other agriculturally acceptable excipient. Compositions comprising natural plant oils such as corn oil and cottonseed oil are effective, and preparations resulting in powders for dusting are particularly useful since the steps required for wetting and drying the fruit are eliminated. When the organisms are grown in a liquid medium, they may be applied in suspension with the liquid medium. Suspensions of the organisms of the invention may also include conventional additives such as surfactants and wetting agents to enhance the effectiveness of the organisms. As an integrated approach, the organisms of the present invention may be used with a very low concentration of a fungicide.

Useful concentrations of suspensions are any concentrations which inhibit the development of the targeted fruit-rot pathogen when applied to the fruit. As will be obvious to one skilled in the art, effective concentrations may vary depending upon such factors as: (1) the type of fruit; (2) the ripeness of the fruit; (3) the concentration of pathogens affecting the fruit; (4) the type of wound on the fruit; (5) temperature and humidity; and (6) the age of the fruit-rot pathogen. Exemplary concentrations range from about $1 \times 10^4$ to $1 \times 10^9$ CFU/ml, most preferably, from about $1 \times 10^7$ to $1 \times 10^9$ CFU/ml. For purposes of the invention, the abbreviation "CFU" is used herein to designate "colony forming units".

The organisms of the invention may be applied to fruit using conventional methods such as dipping, spraying, or brushing. In addition, the organisms of the invention may be incorporated into waxes, wraps or other protective coatings used in processing the fruit.

The fruit may be treated anytime before or after harvest. Typically, the preferred time of treatment is after harvest and prior to storage or shipment.

It is within the scope of the invention to treat the fruit with isolates NRRL Y-18844, NRRL Y-18845 or NRRL Y-18846, alone or in combination (i.e., *C. oleophila* having the identifying characteristics of *C. oleophila* NRRL Y-18844, NRRL Y-18845 or NRRL Y-18846 alone or a mixture of two or more such isolates). The organisms may also be used in combination with other control agents useful for inhibiting the development of fruit-rot pathogens on fruit. When used, these agents should be used in an amount, as readily determined by one skilled in the art, which will not interfere with the effectiveness of the organisms of the invention.

The following examples are intended to further illustrate the invention and not to limit the scope of the invention as defined by the claims.

EXAMPLE 1

The effectiveness of *C. oleophila* (NRRL Y-18844, NRRL Y-18845 and NRRL Y-18846) was evaluated using "Red Delicious" apples. The fruit rot pathogens tested were *Botrytis cinerea* and *Penicillium expansum*, responsible for gray mold and green mold.

Biologically pure cultures of *Candida oleophila* isolates were obtained by using the following procedures: a tomato was dipped in a container of 150 ml sterile deionized water, and the fruit was washed two separate times. Five apples were wounded (3 mm × 5 mm deep). Fifty μl of the first and second washing solution was placed in each wound. After 2 hours the wounds were inoculated with 20 μl of a spore suspension of *Botrytis cinerea* ($1 \times 10^5$ CFU/ml). The fruit were stored in trays at room temperature.

After 10 days, wounds on the inoculated apples not showing rot were scraped with a sterile inoculating needle. Dislodged material was diluted in 10 ml of sterile water, and 100 μl of this suspension was spread on yeast-maltose agar plates. After 1 day, single colonies with different visual appearance were streaked on plates of yeast-maltose agar. After the colonies developed, each was checked microscopically to separate the yeasts and bacteria.

Three isolates of *Candida oleophila* were derived by the method (NRRL Y-18844, NRRL Y-18845 and NRRL Y-18846). These isolates were grown in a liquid yeast maltose medium for 24 hours, and 50 μl of a $1 \times 10^8$ CFU suspension of washed cells was pipetted into apple wounds. After 2 hours, the treated wounds were inoculated with 20 μl of *Botrytis cinerea* or *Penicillium expansum* spores ($1 \times 10^5$ spores/ml). After 14 days the wounds were examined for rot. FIG. 1 summarizes the results. All three isolates effectively controlled both Botrytis and Penicillium rots of apple.

EXAMPLE II

The effectiveness of three isolates of *C. oleophila* (NRRL Y-18844, NRRL Y-18845 and NRRL Y-18846) for inhibiting *Penicillium digitatum* on oranges was tested.

Oranges (*Citrus sinesis*) were washed with 2% sodium hypochlorite to surface sterilize the fruit. After air drying, the oranges were placed on styrofoam trays in plastic trays with lids. Water (100 ml) was added to each tray for humidity. The oranges were wounded using a needle. Wound size was 4 mm wide by 5 mm deep. Three-day-old shake cultures of NRRL Y-18844, NRRL Y-18845 and NRRL Y-18846 growing on NYDB at a $1 \times 10^9$ CFU/ml concentration were added to the wound, 50 μl/wound, and the oranges were allowed to air dry. Thereafter an aqueous suspension of *Penicillium digitatum* ($1 \times 10^4$ spores/ml) were added to the wounds, 20 μl/wound. Controls were inoculated with water only.

Figure 2:
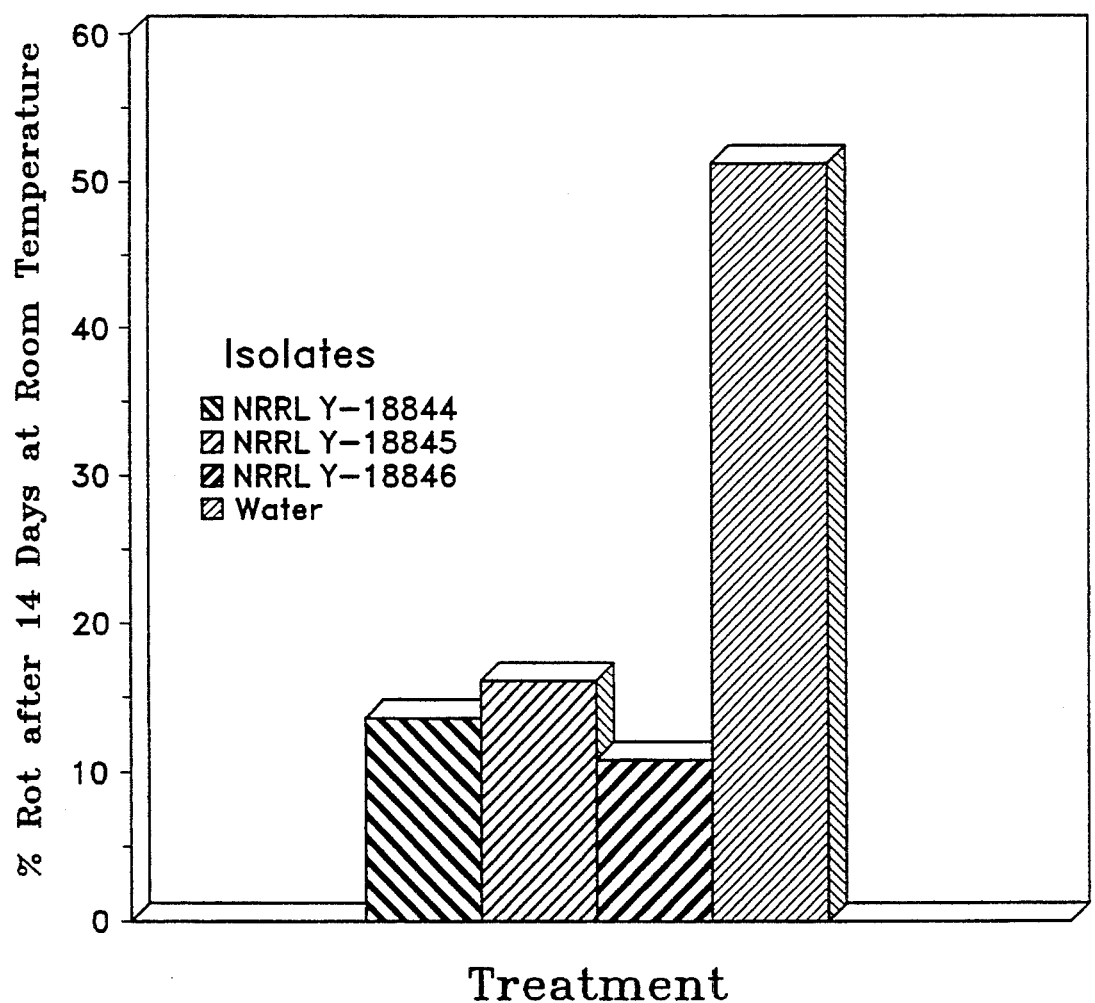
FIG. 2 is a bar graph of percent rot of oranges treated with NRRL Y-18844, NRRL Y-18845 AND NRRL Y-18846 and oranges treated only with water, showing inhibition of *Penicillium digitatum* rot.

All three isolates of *C. oleophila* reduced rot caused by *Penicillium digitatum* as shown in FIG. 2.

EXAMPLE III

The effectiveness of *C. oleophila* isolate NRRL Y-18846 was compared with commercial fungicides for the control of *Monilinia fructicola* and *Rhizopus stolinfer* rots of Candor peaches as postharvest treatments on a semi-commercial packing line. Ten boxes per treatment of peaches (64 peaches per box) were placed on a semi-commercial peach processing line where they were (1) washed and defuzzed; (2) dried; (3) treated with a micronized spray of the antagonist *C. oleophila* (isolate NRRL Y-18846); (4) dried; and (5) waxed.

Four treatments were compared: (1) peaches waxed and not treated with the commercial rate of the fungicides Topsin and Botran; (2) peaches waxed with a preparation which contained the commercial rate of the fungicides Topsin and Botran (1 lb/100 gallons); (3) peaches washed but not waxed or treated with fungicides; and (4) peaches washed, dried, treated with a micronized preparation of *C. oleophila* isolate (NRRL Y-18846), dried and waxed.

Figure 3:
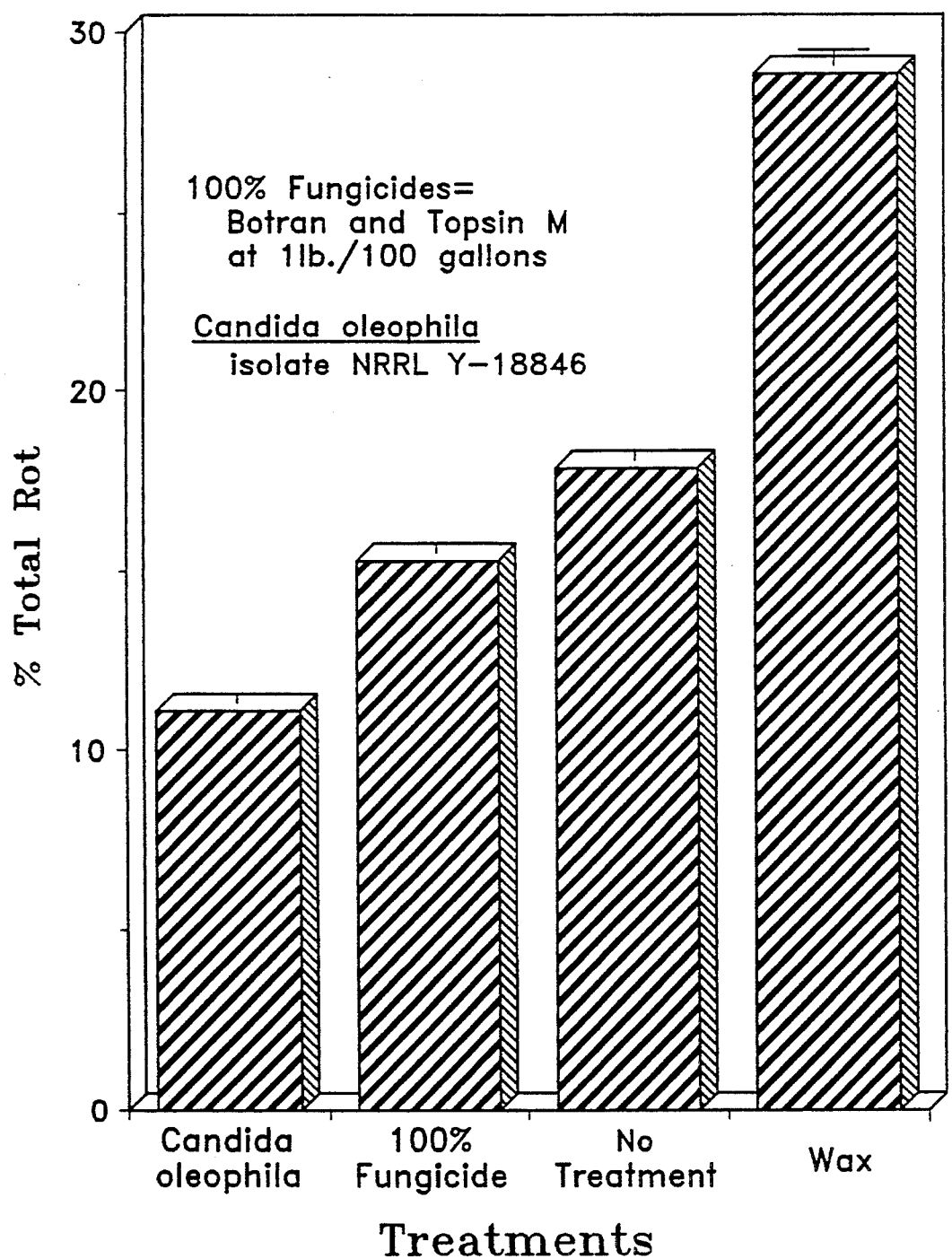
FIG. 3 is a bar graph showing total rot of peaches treated with *Candida oleophila* (NRRL Y-18846) on a semi-commercial packing line as compared with peaches receiving the standard fungicidal treatment.

Following the treatments the peaches were placed in trays and stacked in boxes where they were stored at 10° C. Every 4 days for 16 days the number of rotted fruit was recorded. The results are presented in FIG. 3.

NRRL Y-18846 effectively controlled both Monilia and Rhizopus rots of peaches when applied as a micronized spray on a peach processing line. It provided better protection against rot than commerical fungicide treatments or wax alone.

The foregoing detailed descriptions and examples are given merely for purposes of illustration. Modifications and variations may be made therein without departing from the spirit and scope of the invention.

We claim:

1. A method of controlling postharvest diseases in fruit by applying a biocontrol composition to the fruit, said biocontrol composition comprising an amount of *Candida oleophila* effective for the control of fruit-rot pathogens and an agriculturally acceptable excipient.

2. The method of claim 1, wherein said *Candida oleophila* is NRRL Y-18844, NRRL Y-18845, NRRLY-18846 or a combination of at least two of NRRL Y-18844, NRRL Y-18845 or NRRL Y-18846.

3. The method of claim 1, wherein said *Candida oleophila* is NRRL Y-18844.

4. The method of claim 1, wherein said *Candida oleophila* is NRRL Y-18845.

5. The method of claim 1, wherein said *Candida oleophila* is NRRL Y-18846.

6. The method of claim 1, wherein said *Candida oleophila* is a combination of at least two of NRRL Y-18844, NRRL Y-18845 or NRRL Y-18846.

7. The method of claim 1, wherein said effective amount of biocontrol composition is from about $1 \times 10^4$ CFU/ml to about $1 \times 10^9$ CFU/ml.

8. The method of claim 6, wherein said effective amount of biocontrol composition is from about $1 \times 10^7$ CFU/ml to about $1 \times 10^9$ CFU/ml.

9. The method of claim 1, wherein said fruit-rot pathogens are *Penicillium digitatum, Botrytis cinerea, Rhizopus stolinifer, Penicillium expansum* and *Monilinia fructicola*.

10. The method of claim 1, wherein said agriculturally acceptable excipient is water, natural plant oil or dust.

* * * * *